United States Patent
VanCamp et al.

(10) Patent No.: US 8,118,857 B2
(45) Date of Patent: Feb. 21, 2012

(54) MEDICAL ARTICLES THAT STIMULATE ENDOTHELIAL CELL MIGRATION

(75) Inventors: Daniel VanCamp, Elk River, MN (US); Rajesh Radhakrishnan, Maple Grove, MN (US); Eric Nielson, Bellevue, WA (US); Verivada Chandrasekaran, Mercer Island, WA (US)

(73) Assignee: Boston Scientific Corporation, Maple Grove, MN (US)

( * ) Notice: Subject to any disclaimer, the term of this patent is extended or adjusted under 35 U.S.C. 154(b) by 588 days.

(21) Appl. No.: 11/947,150

(22) Filed: Nov. 29, 2007

(65) Prior Publication Data

US 2009/0143856 A1    Jun. 4, 2009

(51) Int. Cl.
    *A61F 2/82* (2006.01)
(52) U.S. Cl. ...................... 623/1.15; 623/1.49
(58) Field of Classification Search ............... 623/1.46, 623/1.15, 1.11, 1.1, 1.49; 602/41, 43
    See application file for complete search history.

(56) References Cited

U.S. PATENT DOCUMENTS

| | | | |
|---|---|---|---|
| 2,950,187 A | 8/1960 | Ototani | |
| 3,687,135 A | 8/1972 | Stroganov et al. | |
| 4,314,554 A | 2/1982 | Greatbatch | |
| 5,059,211 A | 10/1991 | Stack et al. | |
| 5,306,286 A | 4/1994 | Stack et al. | |
| 5,356,433 A | 10/1994 | Rowland et al. | |
| 5,462,575 A | 10/1995 | Del Corso | |
| 5,628,787 A | 5/1997 | Mayer | |
| 5,632,840 A | 5/1997 | Campbell | |
| 5,676,685 A | 10/1997 | Razavi | |
| 5,891,191 A | 4/1999 | Stinson | |
| 5,957,975 A | 9/1999 | Lafont et al. | |
| 6,174,330 B1 | 1/2001 | Stinson | |
| 6,240,616 B1 | 6/2001 | Yan | |
| 6,287,332 B1 | 9/2001 | Bolz et al. | |
| 6,379,383 B1 | 4/2002 | Palmaz et al. | |
| 6,471,980 B2 | 10/2002 | Sirhan et al. | |
| 6,488,702 B1 | 12/2002 | Besselink | |
| 6,854,172 B2 | 2/2005 | Kaese et al. | |

(Continued)

FOREIGN PATENT DOCUMENTS

CA        1113396    * 12/1981    ............ 167/156

(Continued)

OTHER PUBLICATIONS

John A. Veil, John J. Quinn; "Downhole Separation Technology Performance: Relationship to Geologic Conditions"—Prepared for U.S. Dept. of Energy, National Energy Technology Laboratory under Contrct W-31-109-Eng-38—Argonne National Laboratory—Nov. 2004.

(Continued)

*Primary Examiner* — Thomas J Sweet
*Assistant Examiner* — Matthew Schall
(74) *Attorney, Agent, or Firm* — Fish & Richardson P.C.

(57) ABSTRACT

A medical article that includes (a) an electronically conductive substrate having a specific conductivity of at least 1 μS/cm and (b) a galvanic couple that includes a first member and a second member arranged in sufficient proximity to each other to generate a localized electric field under physiological conditions. The first and second members are selected such that the galvanic couple exhibits an average plateau current density of at least 25 microamps/cm$^2$ when short circuited in a zero resistance ammeter test at room temperature using a saline electrolyte.

19 Claims, 1 Drawing Sheet

U.S. PATENT DOCUMENTS

| | | |
|---|---|---|
| 6,951,053 B2 | 10/2005 | Padilla et al. |
| 6,953,560 B1 | 10/2005 | Castro et al. |
| 7,011,678 B2 | 3/2006 | Tenerz et al. |
| 7,208,172 B2 | 4/2007 | Birdsall et al. |
| 7,335,375 B2 | 2/2008 | Li et al. |
| 7,402,173 B2 | 7/2008 | Scheuermann et al. |
| 7,637,941 B1 | 12/2009 | Manicka et al. |
| 2002/0138131 A1 | 9/2002 | Solovay et al. |
| 2003/0060873 A1 | 3/2003 | Gertner et al. |
| 2004/0034409 A1 | 2/2004 | Heublein et al. |
| 2004/0088038 A1 | 5/2004 | Dehnad et al. |
| 2004/0230225 A1 | 11/2004 | Penner et al. |
| 2005/0222671 A1 | 10/2005 | Schaeffer et al. |
| 2005/0234538 A1 | 10/2005 | Litvack et al. |
| 2006/0015052 A1 | 1/2006 | Crisp |
| 2006/0025848 A1 | 2/2006 | Weber et al. |
| 2006/0052863 A1 | 3/2006 | Harder et al. |
| 2006/0052864 A1 | 3/2006 | Harder et al. |
| 2006/0122694 A1 | 6/2006 | Stinson et al. |
| 2006/0149352 A1 | 7/2006 | Schlun |
| 2006/0198869 A1 | 9/2006 | Furst et al. |
| 2006/0229711 A1 | 10/2006 | Yan et al. |
| 2006/0271168 A1 | 11/2006 | Kleine et al. |
| 2007/0003596 A1 | 1/2007 | Tittelbach et al. |
| 2007/0020306 A1 | 1/2007 | Schultheiss |
| 2007/0050009 A1 | 3/2007 | Flanagan |
| 2007/0055364 A1 | 3/2007 | Hossainy et al. |
| 2007/0135908 A1 | 6/2007 | Zhao |
| 2007/0142899 A1 | 6/2007 | Lootz et al. |
| 2007/0156231 A1 | 7/2007 | Weber |
| 2007/0156248 A1 | 7/2007 | Marco et al. |
| 2007/0178129 A1 | 8/2007 | Flanagan |
| 2007/0191931 A1 | 8/2007 | Weber et al. |
| 2007/0224244 A1 | 9/2007 | Weber et al. |
| 2007/0244569 A1 | 10/2007 | Weber et al. |
| 2007/0270942 A1 | 11/2007 | Thomas |
| 2007/0282432 A1 | 12/2007 | Stinson et al. |
| 2008/0033536 A1 | 2/2008 | Wittchow |
| 2008/0033537 A1 | 2/2008 | Tittelbach |
| 2008/0057105 A1 | 3/2008 | Atanasoska et al. |
| 2008/0058923 A1 | 3/2008 | Bertsch et al. |
| 2008/0071348 A1 | 3/2008 | Boismier et al. |
| 2008/0071349 A1 | 3/2008 | Atanasoska et al. |
| 2008/0071350 A1 | 3/2008 | Stinson |
| 2008/0071351 A1 | 3/2008 | Flanagan et al. |
| 2008/0071352 A1 | 3/2008 | Weber et al. |
| 2008/0071357 A1 | 3/2008 | Girton et al. |
| 2008/0071358 A1 | 3/2008 | Weber et al. |
| 2008/0082162 A1 | 4/2008 | Boismier et al. |
| 2008/0086201 A1 | 4/2008 | Weber et al. |
| 2008/0090097 A1 | 4/2008 | Shaw et al. |
| 2008/0097577 A1 | 4/2008 | Atanasoska et al. |
| 2008/0103594 A1 | 5/2008 | Loffler et al. |
| 2008/0109072 A1 | 5/2008 | Girton |
| 2008/0131479 A1 | 6/2008 | Weber et al. |
| 2008/0147175 A1 | 6/2008 | Krivoruchko et al. |
| 2008/0160259 A1 | 7/2008 | Nielson et al. |
| 2008/0161906 A1 | 7/2008 | Atanasoska et al. |
| 2008/0183277 A1 | 7/2008 | Atanasoska et al. |
| 2008/0183278 A1 | 7/2008 | Atanasoska et al. |
| 2008/0195189 A1 | 8/2008 | Asgari |
| 2008/0215129 A1 | 9/2008 | Venturelli et al. |
| 2009/0012599 A1 | 1/2009 | Broome et al. |
| 2009/0018648 A1 | 1/2009 | Wittchow |
| 2009/0024199 A1 | 1/2009 | Birdsall et al. |
| 2009/0024211 A1 | 1/2009 | Wittchow |
| 2009/0030500 A1 | 1/2009 | Weber et al. |
| 2009/0030506 A1 | 1/2009 | Klocke et al. |
| 2009/0030507 A1 | 1/2009 | Klocke et al. |
| 2009/0048660 A1 | 2/2009 | Adden |
| 2009/0062905 A1 | 3/2009 | Moore, Jr. et al. |
| 2009/0069884 A1 | 3/2009 | Mueller |
| 2009/0076588 A1 | 3/2009 | Weber |
| 2009/0118815 A1 | 5/2009 | Arcand et al. |
| 2009/0157165 A1 | 6/2009 | Miller et al. |
| 2009/0164002 A1 | 6/2009 | Becher et al. |
| 2009/0171452 A1 | 7/2009 | Yamamoto et al. |
| 2009/0192595 A1 | 7/2009 | Nagura et al. |
| 2009/0192596 A1 | 7/2009 | Adden |
| 2009/0196899 A1 | 8/2009 | Birdsall et al. |
| 2009/0208555 A1 | 8/2009 | Kuttler et al. |
| 2009/0214373 A1 | 8/2009 | Stinson et al. |
| 2009/0240323 A1 | 9/2009 | Wilcox |
| 2009/0254171 A1 | 10/2009 | Heikkila |
| 2009/0270979 A1 | 10/2009 | Adden |
| 2009/0281613 A1 | 11/2009 | Atanasoska et al. |
| 2009/0287301 A1 | 11/2009 | Weber |
| 2009/0306756 A1 | 12/2009 | Cho et al. |
| 2009/0306765 A1 | 12/2009 | Weber |
| 2009/0306766 A1 | 12/2009 | McDermott et al. |

FOREIGN PATENT DOCUMENTS

| | | |
|---|---|---|
| EP | 0 923 389 | 7/1997 |
| EP | 1 071 490 | 1/2001 |
| EP | 1 270 023 | 1/2003 |
| EP | 1 370 306 | 12/2003 |
| EP | 1 419 793 | 5/2004 |
| EP | 1 465 552 | 10/2004 |
| EP | 1 562 565 | 8/2005 |
| EP | 1 632 256 | 3/2006 |
| EP | 1 642 551 | 4/2006 |
| EP | 1 653 885 | 5/2006 |
| EP | 1 703 858 | 9/2006 |
| EP | 1 750 780 | 2/2007 |
| EP | 1 835 042 | 9/2007 |
| NL | 7707627 | 7/1978 |
| WO | 99/33410 | 7/1999 |
| WO | WO03/063733 | 8/2003 |
| WO | 2005/025449 | 3/2005 |
| WO | WO2005/023361 | 3/2005 |
| WO | WO2005/030026 | 4/2005 |
| WO | 2006/077154 | 7/2006 |
| WO | 2006/080381 | 8/2006 |
| WO | 2007/013102 | 2/2007 |
| WO | WO2007/013065 | 2/2007 |
| WO | 2007/035791 | 3/2007 |
| WO | 2007/079363 | 7/2007 |
| WO | 2008/092436 | 8/2008 |

OTHER PUBLICATIONS

A.S.G. Curis, "Small is Beautiful But Smaller Is the Aim: Review of a Life of Research", *European Cells and Materials*, vol. 8 2004 (pp. 27-36).

Li and Kolega, "Effects of Direct Current Electric Fields on Cell Migration and Actin Filament Distribution in Bovine Vascular Endothelial Cells", J. Vasc. Res. 2002; 39:391-404.

Authorized officer Simin Baharlou, International Preliminary Report on Patentability in PCT/US08/84960 mailed Jun. 10, 2010, 8 pages.

Aaltonen, "Atomic Layer Deposition of Noble Metal Thin Films," *University of Helsinki*, Apr. 8, 2005, pp. 1-71.

Australian Government, Department of Health and Aging, "Horizon Scanning Technology Prioritising Summary-Biodegradable stents for coronary artery disease," *Australia and New Zealand Horizon Scanning Network (ANZHSN)*, Aug. 2007, pp. 1-13.

Bekesi et al., "Efficient Submircon Processing of Metals with Femto," *Appl. Phys. A.*, Published Oct. 25, 2002, pp. 355-357.

Ben-Hamu et al., "Influence of Si, Ca and Ag addition on corrosion behaviour of new wrought Mg-Zn alloys," *Materials Science and Technology*, 2006, vol. 22, No. 10, pp. 1213-1218.

Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.

Blanusa et al., "Chelators as Antidotes of Metal Toxicity Therapeutic and Experimental Aspects," *Current Medicinal Chemistry*, 2005, vol. 12, pp. 2771-2794.

Bosiers et al., "Absorbable Metal stent for CLI in Infrapopliteal lesions: 1 year results," *CX 2005 Global Endovascular Forum*, Apr. 2005, pp. 1-23.

Brunner et al., "Porosity Tailored Growth of Black Anodic Layers on Magnesium is an Organic Electrolyte," *Journal of the Electrochemical Society*, vol. 156 (2), Dec. 12, 2008, pp. C62-C66.

Chang et al., "Effect of Heat Treatment on Corrosion and Electrochemical behavior of Mg-3Nd-0.2Zn-0.4Zr (wt. %) alloy," *Science Direct, Electrochimica Acta* 52, 2007, 3160-3167.

Chang et al., "Templated sythesis of Gold-iron Alloy nanoparticles using pulsed laser deposition," *Nanotechnology*, vol. 17, 2006, pp. 5131-5135.

Chen et al., "Laser Cladding of Mg20A18o Powder on ZM5 Magnesium Alloy," *Corrosion Engineering, Science and Technology*, 2007, vol. 42, No. 2, pp. 130-136.

Cho et al., "Gold-coated iron nanoparticles: a novel magnetic resonance agent for $T_1$ and $T_2$ weighted imaging," *Nanotechnology*, vol. 17, 2006, pp. 640-644.

Conolly et al., "X-Ray microtomography studies of localized corrosion and transitions to stress corrosion cracking," *Materials Science and Technology*, 2006, vol. 22, No. 9, pp. 1076-1085.

Costa et al., "The effect of the magnetic field on the corrosion behavior of Nd-Fe-B permanent magnets." *Journal of Magnetism and Magnetic Materials*, 278, 2004, pp. 348-358.

De Geest et al., "Self-rupturing Microcapsules," *Adv. Mater.*, 2005, vol. 17, pp. 2357-2361.

Eggebrecht et al., "Novel Magnetic Resonance-Compatible Coronary Stent: The Absorbable Magnesium-Alloy Stent," *Circulation*, 2005, vol. 112, pp. 303-304.

Erbel et al., "Absorbierbare Stents-Eine Vielversprechende Neuerung?" *Urban & Vogel*, No. 4, 2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-1875.

Erne et al., "The Road to Bioabsorbable Stents: Reaching Clinical Reality?" *Cardio Vascular and Interventional Radiology*, Sep. 26, 2005, pp. 11-16.

Falotico, "Cordis Fully Bioabsorbable Stent Program," *Euro PCR09*, May 22, 2009, pp. 1-21.

Fan et al., "Influence of Lanthanum on the microstructure, mechanical property and corrosion resistance of magnesium alloy," *J. Mater Sci*, 2006, vol. 41, pp. 5409-5416.

Fan et al., "Metallic Stents Coated with Bioabsorable Polymers," *Cardiac Interventions Today*, Jun./Jul. 2009, pp. 42-49.

Ferguson et al., "Corrosion—Fatigue Performance of Magnesium Alloys," *International Journal of Modern Physics B*, vol. 17, Nos. 8 & 9, 2003, pp. 1601-1607.

Fischer et al., "Determination of in-vivo corrosion rates of degradable implants by SR-microtomography," date unknown, pp. 1-2.

Fraunhofer, "Prinzip der hochauflösenden Comptuertomographie," Poster, date unknown, 1 page.

Gettleman et al., "Materials Science Measurement of in vivo Corrosion Rates in Baboons, and Correlation with in vitro Tests," *Journal of Dental Research*, 1980, vol. 59, pp. 689-707.

Griffiths et al. "Future Devices: Bioabsorbable stents," *The British Journal of Cardiology (Acute & Interventional Cardiology)*, 2004, vol. 11, pp. 80-84.

Grube, "Bioabsorbable Stents—The Boston Scientific & REVA Technology," *EuroPCR 2009*, 2009, pp. 1-27.

Gu et al., "In vitro Corrosion and biocompatibility of binary magnesium alloys," *Biomaterials*, vol. 30, 2009, pp. 484-498.

Gupta et al., "Nanometer spaced electrodes using selective area atomic layer deposition," *Applied Physics Letters*, vol. 90, 2007, pp. 1-4.

Hänzi et al., "Design strategy for microalloyed ultra-ductile magnesium alloys," *Philosophical Magazine letters*, vol. 89, No. 6, Jun. 2009, pp. 377-390.

Hänzi et al., "Design strategy for new biodegradable Mg-Y-Zn alloys for medical applications," *Int. J. Mat. Res.*, vol. 100, 2009, pp. 1127-1136.

Hänzi et al., "On the biodegradation performance of an Mg-Y-Re alloy with various surface conditions in simulated body fluid," *Acta Biomaterialia*, vol. 5, 2009, pp. 162-171.

Haque et al. "Bioabsorption Qualities of Chitosan-absorbable Vascular Templates," *Current Surgery*, vol. 58, No. 1, Jan./Feb. 2001, pp. 77-80.

Heismann et al., "Density and atomic number measurements with spectral x-ray attenuation method," *Journal of Applied Physics*, vol. 94, No. 3, Aug. 1, 2003, pp. 2073-2079.

Hermawan et al., "Degradable metallic biomaterials: Design and development of Fe-Mn alloys for stents," *Wiley InterScience: Article*, Apr. 19, 2008, pp. 1-12.

Hermawan et al., "Degradation Behaviour of Metallic Biomaterials for Degradable Stents," *Advanced Materials Research*, vols. 15-17, 2007, pp. 113-118.

Hermawan et al., "Development of Degradable Fe-35Mn Alloy for Biomedical Application," *Advanced Material Research*, vols. 15-17 (2007), pp. 107-112.

Hermawan et al., "Fe-Mn Alloys for Metallic Biodegradable Stents: Degradation and Cell Viability Studies," *Acta Biomaterialia*, Manuscript, Mar. 27, 2009, pp. 1-30.

Hermawan, et al., "Iron-Manganese: new class of metallic degradable biomaterials prepared by powder metallurgy," *Powder Metallurgy*, 2008, vol. 51, No. 1, pp. 38-45.

Heublein et al., "Biocorrosion of magnesium alloys: a new principle in cardiovascular implant technology?" *Heart*, 2003, vol. 89, pp. 651-656.

Hildebrandt et al., "Prevention of surface encrustation of urological implants by coating with inhibitors," *Biomaterials*, vol. 22, 2001, pp. 503-507.

Iakovou et al., "Incidence, Predictors, and Outcome of Thrombosis Successful Implantation of Drug-Eluting Stents," *JAMA*, May 4, 2005, vol. 293, No. 17, pp. 2126-2130.

Ignat et al., "Magnesium alloys (WE43 and ZE41) characterization for laser applications," *Applied Surface Science*, vol. 233, 2004, pp. 382-391.

Integran, "Biodegradable Nanometallic Intracoronary Stents," May 12, 2009, 1 page.

Integran, "Biodegradable Nanometallic Intracoronary Stents," *Proposal*, May 12, 2009, 1 page.

Jabara et al., "Bioabsorbable Stents: The Future is Near," *Cardiac Interventions Today*, Jun./Jul. 2009, pp. 50-53.

Jabara, "Poly-anhydride based on salicylic acid and adipic acid anhydride," Glimpse into the future: bioabsorbable stents-aimint to restore vascular integrity, *Euro PCR09*, 2009, pp. 1-34.

Kaesel et al., "Approach to Control the Corrosion of Magnesium by Alloying," *Magnesium: Proceedings of the 6$^{th}$ International Conference Magnesium Alloys and Their Applications*, 2004, pp. 534-539.

Kaya et al., "Microstructure and Corrosion Resistance of Alloys of the Mg-Zn-Ag System," *Metal Science and Heat Treatment*, vol. 48, Nos. 11-12, 2006, pp. 524-530.

Kececioglu, "Zur Biokompatibilitat eines neu entwickelten Stentmaterials aus korrodierbarem Reineisen," Jan. 25, 2007, pp. 1-131, *Ruhr-Universitat-Bochum*.

Kokubo et al., "How useful is SBF in predicting in vivo bone bioactivity?" *Biomaterials*, vol. 27, 2006, pp. 2907-2915.

LaFont, "Arterial Remodeling Technologies: Bioresorbable Stents," *Euro PCR09*, 2009, pp. 1-28.

Levesque et al., "Design of pseudo-physiological test bench specific to the development of biodegradable metallic biomaterials," *Acta Biomaterialia*, vol. 4, 2008, pp. 284-295.

Li et al., "Photoacoustic Tomography and Sensing in Biomedicine," *Phys. Med. Biol.*, vol. 54, 2009, pp. 59-97.

Lu et al., "Theoretical analysis of calcium phosphate precipitation in simulated body fluid," *Biomaterials*, 26, 2005, pp. 1097-1108.

Maeng et al., "Negative Vascular Remodelling after Implantation of Bioabsorbable Magnesium Alloy Stents in Porcine Coronary Arteries: A randomized Comparison with Bare-Metal and Sirolimus-Eluting Stents," *Heart*, 2009, vol. 95, pp. 241-246.

Mandl, "Zerstaubungsabscheidung von Mg-Legierungen," *Leibniz-Institut fur Oberflachenmodifizierung*, 2001, pp. 1-17.

Mani et al., "Coronary Stents: A materials perspective," *Biomaterials*, vol. 28, 2007, pp. 1689-1710.

Markman, "Absorbable Coronary stents," *The Lancet*, vol. 369, Jun. 2, 2007, pp. 1839-1840.

Massaro et al., "Comparative Investigation of the surface properties of commercial titanium dental implants. Part 1: chemical composition," *Journal of Materials Science: Materials in Medicine*, vol. 13, 2002, pp. 535-548.

Miao et al., "Porous Calcium Phosphate Ceramics prepared by coating polyurethane foams with Calcium phosphate cements," *Materials Letters*, vol. 58, 2004, pp. 397-402.

Mueller et al., "Control of smooth muscle cell proliferation by ferrous iron," *Biomaterials*, vol. 27, 2006, pp. 2193-2200.

Muller et al., "Magnesium and its Alloys as Degradable Biomaterials, Corrosion Studies Using Potentiodynamic and EIS Electrochemical Tenchiques," *Materials Research*, vol. 10, No. 1, 2007, pp. 5-10.

Muller et al., "Preparation of SBF with different $HCO_3$ content and its influence on the composition of biomimetic apatites," *Acta Biomaterialia*, vol. 2, 2006, pp. 181-189.

Munoz et al., "Interactive Effects of Albumin and Phosphate Ions on the Corrosion of CoCrMo Implant Alloy," *Journal of the Electrochemical Society*, vol. 154, No. 10, 2007, pp. 562-570.

Nachtrab et al., "Quantitative Material Analysis by Dual-Energy Computed Tomography for Industrial NDT Applications," *Fraunhofer EZRT*, date unknown, 1 page.

Niinisto, "Atomic Layer deposition: A key technology for the controlled growth of oxide thin films for advanced applications," *Proc. Estonian Acad. Sci. Phys. Math.*, 2003, vol. 52, No. 3, pp. 266-276.

Onuma et al., "Everolimus-eluting bioabsorbable stent," *Euro PCR09*, May 22, 2009, pp. 1-28.

Ormiston et al., "Bioabsorbable Coronary Stents," *Circulation Cardiovasc Intervent*, vol. 2, 2009, pp. 255-260.

Ouerd et al., "Reactivity of Titanium in Physiolgoical Medium—I. Electrochemical Characterization of the Metal/Protein Interface," *Journal of the Electrochemical Society*, vol. 154, No. 10, 2007, pp. 593-601.

Oyane et al., "Preparation and assessment of revised simulated body fluids," *Wiley Periodicals, Inc.*, 2003, pp. 188-195.

Peeters, et al., "Preliminary Data on Absorbable Metal Stents," *MEET 2006*, Jun. 2006, pp. 1-30.

Peeters et al., "Preliminary Results after Application of Absorbable Metal Stents in Patients with Critical Limb Ischemia," *J. Endovasc Ther*, 2005, vol. 12, pp. 1-5.

Peuster et al., "A novel approach to temporary stenting: degradable cardiovascular stents produced from corrodible metal-results 6-18 months after implantation into New Zealand white rabbits," *Heart*, 2001, vol. 86, pp. 563-569.

Peuster et al., "Are resorbable implants about to become a reality," *Cardiol Young*, 2006, vol. 16, pp. 107-116.

Peuster et al., "Long-term biocompatibility of a corrodible peripheral iron stent in the porcine descending aorta," *Biomaterials*, vol. 27, 2006, pp. 4955-4962.

Pinto Slattow et al., "Optical coherence tomography and intravascular untrasound imaging of bioabsorbable magnesium stent degradation in porcine coronary arteries," *Cardiovascular Revascularization Medicine 9*, (2008) pp. 248-254.

Qureshi et al., "The emerging role of iron, zinc, copper, magnesium and selenium and oxidative stress in health and diseases," *Biogenic Amines*, vol. 19, No. 2, 2005, pp. 147-169.

Rettig et al., "Corrosion resistance studies on grain-boundary etched drug-eluting stents," *J. Mater Sci: Mater Med.*, 2007, vol. 18, pp. 1377-1387.

Rettig et al., "Composition of corrosion layers on a magnesium rare-earth alloy in simulated body fluids," *Journal of Biomedical Materials Research Part A*, Oct. 18, 2006, pp. 359-369.

Rettig et al., "Time-dependent electrochemical characterization of the corrosion of a magnesium rare-earth alloy in simulated body fluids," *Journal of Biomedical Materials Research Part A*, 2007, 167-175.

Rinkevich et al., "Regeneration of Amputated Avian Bone by a Coral Skeletal Implant," *Biol. Bull.*, vol. 197, Aug. 1999, pp. 11-13.

Schinhammer et al., "Design strategy for biodegradable Fe-based alloys for medical applications," *Acta Biomaterialia*, 2009, pp. 1-9.

Schranz et al., "Bioabsorbable Metal Stents for Percutaneous Treatment of Critical Recoarctation of the Aorta in a Newborn," *Catheterization and Cardiovascular Interventions*, vol. 67, 2006, pp. 671-673.

Serruys, "Fourth Annual American College of Cardiology International Lecture," *Journal of the American College of Cardiology*, 2006, vol. 47, No. 9, pp. 1754-1768.

Serruys, "Glimpse into the future: bioabsorbable stents-aiming to restore vascular integrity—Introduction & Objectives," *Euro PCR09*, May 18, 2009, pp. 1-4.

Serruys, "Glimpse into the future: bioabsorbable stents-aiming to restore vascular integrity—Take-Home Messages," *Euro PCR09*, May 18, 2009, pp. 1-4.

Shaw, "Corrosion Resistance of Magnesium Alloys," *ASM International*, date unknown, pp. 1-6.

Sieber, et al., "Investigations on the passivity of iron in borate and phosphate buffers, pH 8.4," *Corrosion Science*, vol. 48, 2006, pp. 3472-3488.

Singh Raman et al., "Laser assisted modification of surface microstructure for localised corrosion resistance of magnesium alloys," *Surface Engineering*, 2007, vol. 23, No. 2, pp. 107-111.

Su et al., "Photoacoustic imaging of coronary artery stents," *Optics Express*, vol. 17, No. 22, Oct. 26, 2009, pp. 1-8.

Uhlmann et al., "Schnelle 3D-Analyse von Gefügemerkmalen" *Druckguss*, Apr. 2009, pp. 1-5.

Van Alst, "Potential conflicts of interest," *Euro PCR09*, 2009, pp. 1-22.

Virtanen, "Corrosion of Biomedical Implant Materials," *Corrosion of Biomedical Implant Materials*, vol. 26, Nos. 2-3, 2008, pp. 147-171.

Virtanen et al., "Electrochemical Behavior of Fe in Phosphate Solutions Studied by In Situ X-Ray Absorption Near Edge Structure," *Journal of the Electrochemical Society*, vol. 146, No. 11, 1999, pp. 4087-4094.

Virtanen et al., "Special modes of corrosion under physiological and simulated physiological conditions," *Acta Biomaterialia*, vol. 4, 2008, pp. 468-476.

Volkova, "Effect of Deformation and Heat Treatment on the Structure and Properties of Magnesium Alloys of the Mg-Zn-Zr System," *Metal Science and Heat Treatment*, vol. 48, Nos. 11-12, 2006, pp. 508-512.

Volynova et al., "Mechanical Properties and the Fine Structure of Powdered Iron-Manganese Alloys," *Plenum Publishing Corp.*, 1987, pp. 999-1006.

Waksman, Ron, "Why Bioabsorbale Stent Technology," Glimpse to the Future, *Euro PCR09*, 2009, pp. 1-16.

Waksman, Ron, "Current state of the metallic bioabsorbable stent," Glimpse to the Future, *Euro PCR09*, 2009, pp. 1-24.

Waksman et al., "Early-and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, pp. 1-9.

Waksman et al., "Safety and Efficacy of Bioabsorbable Magnesium Alloy Stents in Procine Coronary Arteries," *Catherterization and Cardiovascular Intervnetions*, 2006, vol. 68, pp. 607-617.

Waksman et al., "Short-term Effects of Biocorrodible Iron Stents in Porcine Coronary Arteries," *Journal of Interventional Cardiology*, vol. 21, No. 1, 2008, pp. 15-20.

Waksman, "Update on Bioabsorbable Stents: From Bench to Clinical," *Journal of Interventional Cardiology*, vol. 19, No. 5, 2006, pp. 414-421.

Wilcox, "Biodegradable Technology: Medtronic Biodegradable Stent Program," *Euro PCR09*, 2009, pp. 1-25.

Windecker et al., "Biolimus-eluting stent with biodegradable polymer versus sirolimus-eluting stent with durable polymer for coronary revascularisations (LEADRERS): a randomized non-inferiority trial," *The Lancet*, Sep. 1, 2008, pp. 1-11.

Witte et al., "Biodegradable magnesium-hydroxyapatite metal matrix composites," vol. 28, 2007, pp. 2163-2174.

Witte et al., "In vitro and in vivo corrosion measurements of magnesium alloys," *Biomaterials*, vol. 27, 2006, pp. 1013-1018.

Witte et al., "In Vivo Corrosion of Four Magnesium Alloys and the Associated Bone Response," *Biomaterials*, vol. 26, 2005, pp. 3557-3563.

Witte, "Magnesium Corrosion: a New Challaenge for temporary Biomaterials," *Laboratory for Biomechanic and Biomaterials*, 2009, pp. 1-20.

Xu et al., "In Vivo corrosion behaviouc of Mg-MnZn alloy for bone implant application," *Journal of Biomedical Materials Research Part A*, Jun. 4, 2007, pp. 703-711.

Yuen et al., "Findings from an Accelerated in Vivo Corrosion Model of Magnesium," *Department of Orthopaedics and Traumatology*, date unknown, pp. 1-2.

Yun et al., "Revolutionizing Biodegradable Materials," *Materials Today*, Oct. 2009, vol. 12, No. 10, pp. 1-11.

Zberg et al., "MgZnCa glasses without clinically observable hydrogen evolution for biodegradable implants," *Nature materials*, Sep. 27, 2009, vol. 8, pp. 887-891.

Zheng, "Symposium on Biodegradable/Biocorroded metallic materials," Nov. 24, 2009, pp. 1-74.

Zhu et al., "Biocompatibility of Fe-O films synthesized by plasma immersion ion implantation and deposition," *Surface and Coatings Technology*, vol. 203, 2009, pp. 1523-1529.

Zhu et al., "Biocompatibility of pure iron: In Vitro assessment of degradation kinetics and cytotoxicity on endothelial cells," *Materials Science and Engineering*, vol. 29, 2009, pp. 1589-1582.

Zucchi et al., "Electrochemical behaviour of a magnesium alloy containing rare earth elements," *Journal of Applied Electrochemistry*, 2006, vol. 36, pp. 195-204.

\* cited by examiner

MEDICAL ARTICLES THAT STIMULATE ENDOTHELIAL CELL MIGRATION

TECHNICAL FIELD

This invention relates to stimulating endothelial cell migration in medical articles.

BACKGROUND

Endothelial cells promote healing of damaged blood vessels within the body by promoting angiogenesis. In addition, endothelial cells can inhibit platelet adhesion and thrombus formation on blood-contacting surfaces. Directional or accelerated endothelial cell migration can be stimulated through application of an electric field.

SUMMARY

There is described a medical article that includes (a) an electronically conductive substrate having a specific conductivity of at least 1 µS/cm and (b) a galvanic couple that includes a first member and a second member arranged in sufficient proximity to each other to generate a localized electric field under physiological conditions. The galvanic couple is chosen based upon the current density observed upon short circuiting at room temperature in 0.9% saline. Galvanic couples exhibiting a current density of at least 25 microamps/cm$^2$ are useful. The galvanic current is measured using the zero resistance ammeter method. In this test, each member of the couple is provided in the form of a foil measuring 5 cm×5 cm, and included in a cell with 0.9% saline solution. The foils are spaced 4 cm apart. The cell is then short circuited and the current density on each foil measured at room temperature. The average of the two current density values is the average plateau current density of the galvanic couple.

The members of the galvanic couple act as electrodes, and could generate a localized electric field in the presence of ion-containing fluids such as plasma and blood. The localized electric field could promote endothelial cell migration under physiological conditions that the article would encounter upon implantation within a patient's body (in the case of implantable medical devices) or on the surface of the patient's body (in the case of external wound healing articles), thus eliminating the need for an external voltage source. Endothelializing the surface of the article, in turn, could promote healing. By selectively placing the members of the galvanic couple on the device, the pattern of endothelialization could be controlled.

As used herein, "metal" means both elemental metals and compounds such as oxides, chlorides, carbonates, and the like.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1:
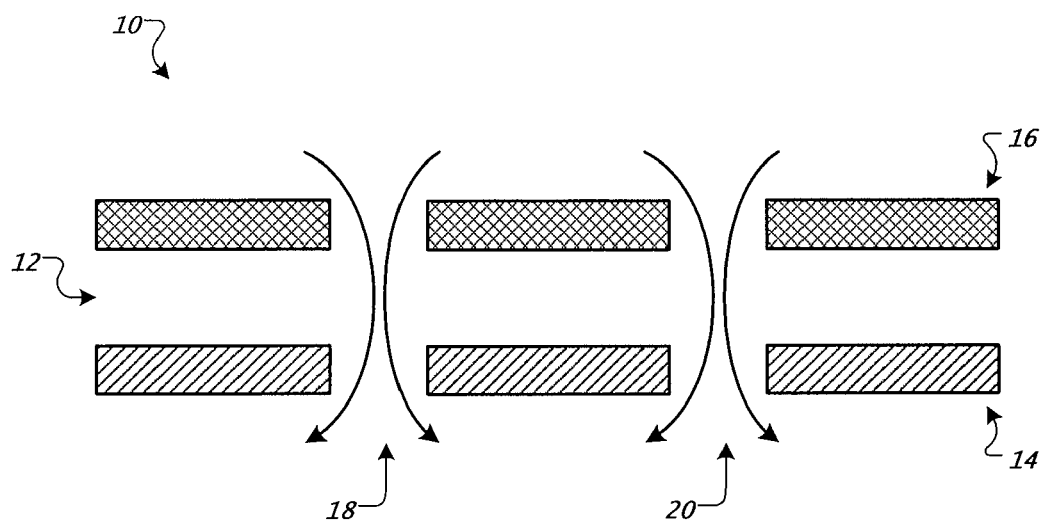
FIG. 1 is a cross-sectional view of an implantable medical device having a porous structure that includes a galvanic couple.

There is described a medical article that includes an electronically conductive substrate having a specific conductivity of at least 1 µS/cm, and a galvanic couple, as described in the Summary, above. The galvanic couple, in the presence of ion-containing fluids such as plasma a blood, forms an electrochemical cell in which the members of the couple act as electrodes and the fluid acts as an ion-conducting electrolyte. The localized electric field that the cell generates could promote endothelial cell migration under physiological conditions, thereby effecting selective placement of endothelial cells on designated portions of the surface of the medical article. Examples of suitable medical articles include implantable articles such as stents, vascular grafts, heart valves, and indwelling catheters. Other examples of suitable medical articles include external wound healing articles such as bandages and wound dressings.

The electronically conductive substrate, as noted above, has a specific conductivity of at least 1 µS/cm, and could be at least 1 mS/cm. Examples of suitable materials for the substrate could include metals (e.g., stainless steel, cobalt-chromium alloys, platinum enhanced stainless steel alloys, Nitinol alloys, and the like), electrically conductive polymers (e.g., polyvinylidene fluoride, polyaniline, and the like), and electrically conductive polymer composites (e.g., polymer matrices containing electrically conductive particles, wires, meshes, or the like).

The members of the galvanic couple are selected with the objective of maximizing the strength of the localized electric field. This objective could be achieved by selecting the members of the galvanic couple such that the couple exhibits an average plateau current density of at least 25 microamps/cm$^2$ (preferably at least 250 microamps/cm$^2$) when short circuited according to the zero resistance ammeter test described in the Summary, above. Such current densities, in turn, could be achieved by selecting the members of the galvanic couple such that the first member of the galvanic couple is less electrochemically active than the second member of the galvanic couple.

Suitable materials for the first member of the galvanic couple could include, for example, noble metals such as platinum, iridium, and ruthenium, as well as oxides of these metals (e.g., iridium oxide). Other examples could include refractory metals such as titanium, hafnium, zirconium, and niobium, and oxides thereof. Suitable materials for the second member of the galvanic couple could include, for example, alkali metals, alkaline earth metals (e.g., magnesium or calcium), transition metals such as zinc, as well as compounds of these metals such as oxides, carbonates, chlorides, and the like. Specific examples of suitable galvanic couples could include:

(a) Pt/Zn;
(b) Iridium Oxide/Zn;
(c) Iridium Oxide/Mg; and
(d) Ruthenium Oxide/Zn.

When the Pt/Zn couple was evaluated in the zero resistance ammeter test, a current density of 0.07 mA/cm$^2$ was measured on the platinum foil and a current density of 0.35 mA/cm$^2$ was measured on the zinc foil, yielding an average plateau current density of 0.21 mA/cm$^2$ (210 µA/cm$^2$).

One or both members of the galvanic couple could be deposited on the electronically conductive substrate using a variety of techniques, including electrodeposition, electrochemical metallization, PVD, CVD, IBAD, FIB, micro-contact printing, self assembly, micro-molding in capillaries, e-beam lithography, photolithography, and the like. Alternatively, one or both members of the galvanic couple could be provided in the form of particles, meshes, or foils. The particles, meshes, and foils, in turn, could be embedded within a matrix.

FIG. 1 illustrates one embodiment of a medical article incorporating a galvanic couple on an electronically conductive substrate. As shown in FIG. 1, medical article 10 includes an electronically conductive substrate 12 (e.g., a polymer such as polyvinylidene fluoride or a porous metal). The inner surface of substrate 12 is provided with the first member 14 of a galvanic couple (e.g., a platinum or iridium oxide layer), while the outer surface of substrate 12 is provided with the second member 16 of the galvanic couple (e.g., a zinc layer). Substrate 12 also includes a plurality of pores 18, 20. When article 10 is in contact with physiological fluids such as blood or saline (e.g., when the article is implanted within a patient's body), current could flow between members 16 and 14 (as shown by the arrows in FIG. 1). The current flow, in turn, could stimulate endothelial cell migration from, e.g., surrounding vessel walls to deposit the cells on the inner surface of substrate 12.

Figure 2:
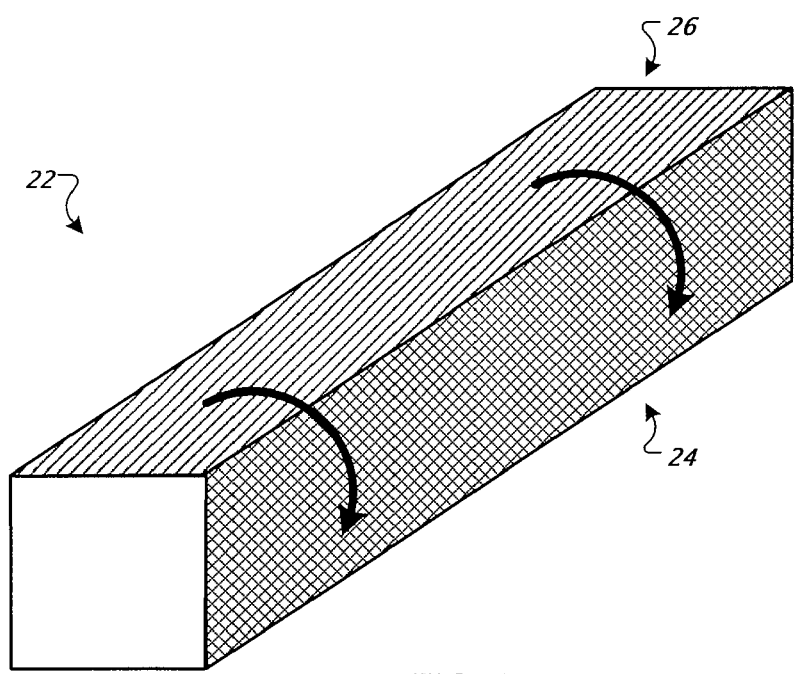
FIG. 2 is a perspective view of a strut of a stent that includes a galvanic couple.

FIG. 2 illustrates another embodiment in which a stent strut 22 is provided on one surface with the first member 24 of a galvanic couple (e.g., a conformal iridium oxide layer) and on another surface with the second member 26 of the galvanic couple (e.g., a zinc layer). Upon exposure to blood or plasma, current could flow between members 26 and 24 (as shown by the arrows in FIG. 2) to deposit endothelial cells on strut 22.

In the case of medical articles such as wound dressings or bandages designed for external application, the members of the galvanic couple could be provided in the form of fibers or particles incorporated within the dressing or bandage. For example, the fibers could be interwoven with the fibers of a gauze pad. Alternatively, the members could be incorporated in semi-porous pouches. The dressing or bandage could further include a conductive gel to improve current flow.

The members of the galvanic couple could be arranged on the medical article in the form of a pattern. By adjusting the shape and dimensions of the pattern, it may be possible to deposit endothelial cells on specific, pre-determined portions of the medical article. The members could be deposited along the entire length or surface of the medical article, or confined to specific portions of the article. In addition, more than one type of galvanic couple could be incorporated in the article.

A number of embodiments have been described. Nevertheless, it will be understood that various modifications may be made without departing from the spirit and scope of the invention. Accordingly, other embodiments are within the scope of the following claims.

What is claimed is:

1. An implantable medical device comprising a stent, the stent including a plurality of stent struts, wherein at least one of the plurality of stent strut comprises:
   (a) an electronically conductive substrate having a specific conductivity of at least 1 μS/cm, the substrate comprising an inner surface, an outer surface, and two opposite side surfaces; and
   (b) a galvanic couple that comprises a first member arranged on the inner surface or one of the two opposite side surfaces and a second member arranged on the outer surface in sufficient proximity to each other to generate a localized electric field under physiological conditions sufficient to stimulate endothelial cell migration from tissue surrounding the outer surface and deposit cells on the inner surface or one of the two opposite side surfaces when the device is implanted, wherein the first and second members are selected such that the galvanic couple exhibits an average plateau current density of at least 25 microamps/cm$^2$ when short circuited in a zero resistance ammeter test at room temperature using a saline electrolyte.

2. An implantable medical device according to claim 1 wherein the first and second members are selected such that the galvanic couple exhibits an average plateau current density of at least 250 microamps/cm$^2$ when short circuited in a zero resistance ammeter test at room temperature using a saline electrolyte.

3. An implantable medical device according to claim 1 wherein the substrate has a specific conductivity of at least 1 mS/cm.

4. An implantable medical device according to claim 1 wherein the first member of the galvanic couple comprises a noble metal.

5. An implantable medical device according to claim 4 wherein the noble metal is selected from the group consisting of platinum, iridium, ruthenium, and combinations thereof.

6. An implantable medical device according to claim 1 wherein the first member of the galvanic couple comprises a refractory metal.

7. An implantable medical device according to claim 6 wherein the refractory metal is selected from the group consisting of titanium, hafnium, zirconium, and niobium, and combinations thereof.

8. An implantable medical device according to claim 1 wherein the second member of the galvanic couple is a metal selected from the group consisting of alkali metals, alkaline earth metals, zinc, and combinations thereof.

9. An implantable medical device according to claim 8 wherein the second member of the galvanic couple comprises zinc.

10. An implantable medical device according to claim 1 wherein the first member of the galvanic couple is selected from the group consisting of platinum, iridium, ruthenium, and combinations thereof, and the second member of the galvanic couple is selected from the group consisting of zinc, magnesium, and combinations thereof.

11. An implantable medical device according to claim 1 wherein the substrate is selected from the group consisting of metals, electrically conductive polymers, electrically conductive polymer composites, and combinations thereof.

12. An implantable medical device
   comprising a stent, the stent including a plurality of stent struts, wherein at least one of the plurality of stent strut comprises:
   (a) an electronically conductive substrate having a specific conductivity of at least 1 μS/cm, wherein the substrate comprises an outer surface, an inner surface, and pores extending between the outer and inner surfaces; and
   (b) a galvanic couple that comprises a first member and a second member arranged in sufficient proximity to each other to generate a localized electric field under physiological conditions, wherein the first and second members are selected such that the galvanic couple exhibits an average plateau current density of at least 25 microamps/cm$^2$ when short circuited in a zero resistance ammeter test at room temperature using a saline electrolyte, wherein one of the members of the galvanic couple is provided on the outer surface of the substrate and the other member of the galvanic couple is provided on the inner surface of the substrate.

13. An implantable medical device according to claim 1 wherein the one of the members of the galvanic couple is provided in the form of a layer deposited on the substrate and the other member of the galvanic couple is provided in the form of particles in a matrix deposited on the substrate.

14. An implantable medical device according to claim 13 wherein the matrix comprises a biodegradable polymer or metal matrix.

15. An implantable medical device according to claim 1 wherein the first and second members of the galvanic couple are deposited on the substrate in the form of a pattern along the length of the article.

16. An implantable medical device according to claim 1 wherein the implantable medical device is a stent.

17. An implantable medical device according to claim 1 wherein the implantable medical device is a vascular graft.

18. An implantable medical device comprising a stent, the stent including a plurality of stent struts, wherein at least one of the plurality of stent strut comprises:
   (a) an electronically conductive substrate having a specific conductivity of at least 1 mS/cm selected from the group consisting of metals, electrically conductive polymers, electrically conductive polymer composites, and combinations thereof, the substrate comprising an inner surface, an outer surface, and two opposite side surfaces; and
   (b) a galvanic couple that comprises a (i) first member selected from the group consisting of platinum, iridium, ruthenium, and combinations thereof, and (ii) a second member selected from the group consisting of zinc, magnesium, and combinations thereof, wherein the first member is arranged on the inner surface or on one of the two opposite side surfaces and the second members is arranged on the outer surface in sufficient proximity to each other to generate a localized electric field under physiological conditions sufficient to stimulate endothelial cell migration from tissue surrounding the outer surface and deposit cells on one of the inner surface or on one of the two opposite side surfaces when the device is implanted, and the first and second members are selected such that the galvanic couple exhibits an average plateau current density of at least 250 microamps/cm$^2$ when short circuited in a zero resistance ammeter test at room temperature using a saline electrolyte.

19. An implantable medical device according to claim 18 wherein the device is a stent.

* * * * *

UNITED STATES PATENT AND TRADEMARK OFFICE
CERTIFICATE OF CORRECTION

| | | |
|---|---|---|
| PATENT NO. | : 8,118,857 B2 | Page 1 of 1 |
| APPLICATION NO. | : 11/947150 | |
| DATED | : February 21, 2012 | |
| INVENTOR(S) | : VanCamp et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 471 days.

Signed and Sealed this
Twenty-fourth Day of July, 2012

David J. Kappos
*Director of the United States Patent and Trademark Office*